United States Patent [19]

Heymes et al.

[11] Patent Number: 4,476,124
[45] Date of Patent: Oct. 9, 1984

[54] 2-AMINO-4-THIAZOLYL-2-OXYIMINO-ACETAMIDO-BICYCLOOCTENE-CARBOXYLIC ACIDS

[75] Inventors: René Heymes, Vesoul; Alain Bonnet, Livry-Gargan; Didier Pronine, Rosny-sous-Bois, all of France

[73] Assignee: Roussel Uclaf, Paris, France

[21] Appl. No.: 377,597

[22] Filed: May 12, 1982

[30] Foreign Application Priority Data

May 13, 1981 [FR] France ................... 81 09515

[51] Int. Cl.³ ............... C07D 417/12; A61K 31/54
[52] U.S. Cl. ........................... 424/246; 544/47
[58] Field of Search ..................... 544/47; 424/246

[56] References Cited

U.S. PATENT DOCUMENTS 4,103,086  7/1978  Gleason et al. ............. 544/47

FOREIGN PATENT DOCUMENTS 2313065 12/1976 France .
2324639  4/1977 France .
2385722 10/1978 France .

OTHER PUBLICATIONS

Douglas et al.; Canadian Jour. of Chemistry, vol. 56, pp. 2879-2883, (1978).
Doyle et al., Canadian Jour. of Chemistry, vol. 58, pp. 2508-2523, (1980).

Primary Examiner—John M. Ford
Attorney, Agent, or Firm—Charles A. Muserlian

[57] ABSTRACT

Novel syn isomers of optically active isomers and racemates of 7-[2-(2-amino-4-thiazolyl)-2-oxyiminoacetamido]-bicyclooctene-carboxylic acid derivatives of the formula

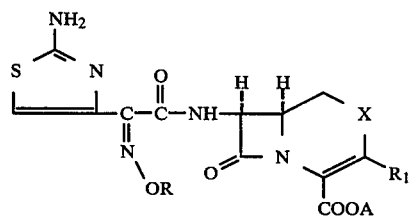

wherein R is selected from the group consisting of hydrogen, optionally substituted alkyl of 1 to 6 carbon atoms and optionally substituted alkenyl and alkynyl of 2 to 6 carbon atoms, $R_1$ is selected from the group consisting of hydrogen, methyl, halomethyl, hydroxymethyl and acyloxymethyl, X is selected from the group consisting of oxygen and optionally oxidized sulfur, A is selected from the group consisting of hydrogen, an alkali metal, —$NH_4$, alkaline earth metal equivalent, a non-toxic, pharmaceutically acceptable organic amine and an easily cleavable ester group and their non-toxic, pharmaceutically acceptable acid addition salts having antibiotic activity and their preparation.

16 Claims, No Drawings

2-AMINO-4-THIAZOLYL-2-OXYIMINO-ACETAMIDO-BICYCLOOCTENE-CARBOXYLIC ACIDS

STATE OF THE ART

French patent No. 2 385 722 describes compounds containing in position 1, but not in position 2, a sulfur atom, an oxygen atom or a group —CH$_2$— or —NH—. French patent Nos. 2 313 065 and 2 324 639 describe compounds containing in position 2 respectively an oxygen atom and a sulfur atom, but the acyl radical in position 7 of the compounds of the present invention are neither described nor suggested in these patents.

OBJECTS OF THE INVENTION

It is an object of the invention to provide the novel compounds of formula I and their non-toxic, pharmaceutically acceptable acid addition salts and a novel process and intermediates for their preparation.

It is another object of the invention to provide novel antibiotic compositions and to provide a novel method of combatting bacterial infections in warm-blooded animals.

These and other objects and advantages of the invention will become obvious from the following detailed description.

THE INVENTION

The novel compounds of the invention are selected from the group consisting of syn isomers of optically active isomers and racemates of 7-/2-(2-amino-4-thiazolyl)-2-oxy-imino-acetamido/-bicyclooctene-carboxylic acid derivatives of the formula

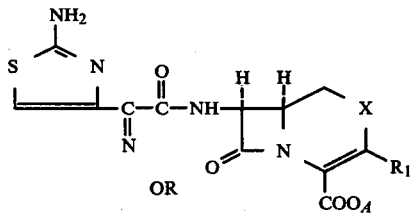

wherein R is selected from the group consisting of hydrogen, optionally substituted alkyl of 1 to 6 carbon atoms and optionally substituted alkenyl and alkynyl of 2 to 6 carbon atoms, R$_1$ is selected from the group consisting of hydrogen, methyl, halomethyl, hydroxymethyl and acyloxymethyl, X is selected from the group consisting of oxygen and optionally oxidized sulfur, A is selected from the group consisting of hydrogen, an alkali metal, —NH$_4$, alkaline earth metal equivalent, a non-toxic, pharmaceutically acceptable organic amine and an easily cleavable ester group and their non-toxic, pharmaceutically acceptable acid addition salts.

Examples of R are hydrogen; alkyl such as methyl, ethyl, propyl, isopropyl, butyl, sec.-butyl, tert.-butyl, pentyl, isopentyl, sec.-pentyl, tert.-pentyl, neo-pentyl, hexyl, isohexyl, sec.-hexyl and tert.-hexyl; alkenyl such as vinyl, allyl, 1-propenyl, butenyl, pentenyl and hexenyl; and alkynyl such as ethynyl, propargyl and butynyl.

The said aliphatic groups of R may be substituted with at least one group such as optionally salified or esterified carboxyl, alkoxycarbonyl such as methoxycarbonyl, or ethoxycarbonyl, carbamoyl, dimethylcarbamoyl, amino, dialkylamino of 1 to 6 alkyl carbons such as dimethylamino or diethylamino, alkylamino of 1 to 6 alkyl carbons such as methylamino, halogens such as chlorine, bromine or iodine, alkoxy and alkylthio of 1 to 6 carbon atoms such as methoxy, ethoxy, propoxy, methylthio, ethylthio, and propylthio, aryl such as phenyl, heterocyclic aryl such as tetrazolyl, arylthio such as optionally substituted phenylthio, heterocyclic arylthio such as optionally alkyl substituted tetrazolylthio and thiadiazolylthio wherein the alkyl is 1 to 6 carbon atoms such as methyl.

Examples of R$_1$ are hydrogen, methyl, hydroxymethyl, halomethyl such as chloromethyl and bromomethyl and acyloxymethyl of an organic carboxylic acid of 1 to 7 carbon atoms such as acetoxymethyl and propionyloxymethyl. Examples of X are —O— and —S— and $\alpha$-sulfoxide, $\beta$-sulfoxide and sulfone.

Examples of A are hydrogen, alkali metal such as sodium, potassium and lithium, alkaline earth metals such as calcium, magnesium, —NH$_4$, an organic amine such as methylamine, propylamine, trimethylamine, diethylamine, triethylamine, N,N-dimethyl-ethanolamine, tris-(hydroxymethyl)-aminomethane, ethanolamine, pyridine, picoline, dicyclohexylamine, morpholine, benzylamine, procaine, lysine, arginine, histidine and N-methylglucamine or an easily cleavable ester.

Examples of easily cleavable esters of A are methoxymethyl, ethoxymethyl, isopropyloxymethyl, $\alpha$-methoxyethyl, $\alpha$-ethoxyethyl, methylthiomethyl, ethylthiomethyl, isopropylthiomethyl, pivaloyloxymethyl, acetoxymethyl, propionyloxymethyl, butyryloxymethyl, isobutyryloxymethyl, valeryloxymethyl, isovaleryloxymethyl, propionyloxyethyl, isovaleryloxyethyl, 1-acetoxyethyl, 1-acetoxypropyl, 1-acetoxyhexyl, 1-acetoxyheptyl, phthalidyl, 5,6-dimethylphthalidyl, methoxycarbonyloxymethyl, 1-methoxycarbonyloxyethyl and 1-ethoxycarbonyloxyethyl.

Examples of suitable acids for the non-toxic, pharmaceutically acceptable acid addition salts are inorganic acids such as hydrochloric acid, hydrobromic acid, nitric acid, sulfuric acid and phosphoric acid and organic acids such as acetic acid, trifluoroacetic acid, maleic acid, tartaric acid, oxalic acid, methanesulfonic acid, benzenesulfonic acid and p-toluenesulfonic acid.

The compounds of formula I may also be present in the form of their internal salts.

Among the preferred compounds of formula I are those wherein R is hydrogen or alkyl of 1 to 3 carbon atoms optionally substituted with carboxyl which may be free, salified or esterified or with —NH$_2$, those wherein X is sulfur and those wherein R$_1$ is hydrogen and their non-toxic, pharmaceutically acceptable acid addition salts.

Preferred specific compounds of the invention are the syn isomers of 7-[2-(2-amino-4-thiazolyl)-2-methoxyimino-acetamido]-8-oxo-4-thia-1-azabicyclo [4,2,0] oct-2-ene-2-carboxylic acid, 7-[2-(2-amino-4-thiazolyl)-2-hydroxyimino-acetamido]-8-oxo-4-thia-1-azabicyclo [4,2,0] oct-2-ene-2-carboxylic acid and 7-[2-(2-amino-4-thiazolyl)-2-carboxymethoxyiminoacetamido]-8-oxo-4-thia-1-azabicyclo [4,2,0] oct-2-ene-2-carboxylic acid in their optically active or racemic mixture form and their alkali metal, alkaline earth metal, ammonium and organic amine salts and their easily cleavable esters.

The compounds of formula I may have the form indicated in formula I or in the form of compounds of the formula

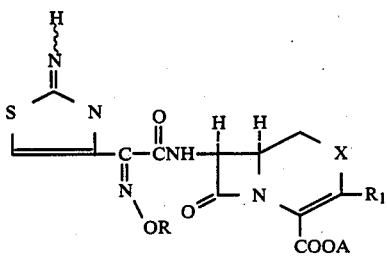

wherein R, R₁, A and X have the above definitions. Moreover, the compounds of formula I all have the cis isomeric form and are numbered as follows

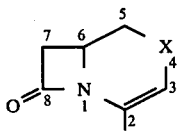

in accordance with U.S. Pat. No. 4,166,816 and the racemic products are designated as (6RS,7RS).

The novel process of the invention for the preparation of the compounds of formula I comprises reacting an optically active isomer or racemic mixture of a compound of the formula

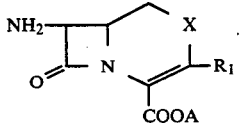

wherein X, R₁ and A have the above definition with an acid of the formula

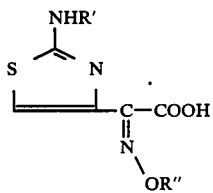

or a functional derivative thereof where R' is selected from the group consisting of hydrogen and an amino protective group and R" is selected from the group consisting of an hydroxyl protective group and R to obtain a racemic mixture or optically active isomer of a compound of the formula

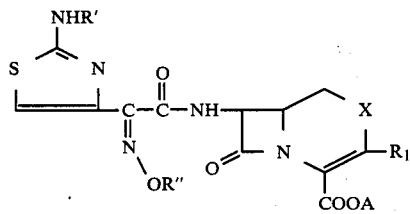

and optionally subjecting the latter to at least one of the following reactions in the desired order (a) subjecting the latter to hydrolysis, hydrogenolysis or to thiourea to remove all or part of the ester groups or protective groups, (b) esterification or salification with a base of the carboxyl groups, (c) salification with a non-toxic, pharmaceutically acceptable acid of the amino groups and (d) resolution of the compound to obtain the optically active isomer.

In the said process, an easily removable ester group of A may be an ester formed with butyl, isobutyl, tert.-butyl, pentyl, hexyl, acetoxymethyl, propionyloxymethyl, butyryloxymethyl, valeryloxymethyl, pivaloyloxymethyl, 2-acetoxyethyl, 2-propionyloxyethyl, 2-butyryloxyethyl, 2-iodoethyl, β,β,β-trichloroethyl, vinyl, allyl, ethynyl, propynyl, benzyl, 4-methoxybenzyl, 4-nitrobenzyl, phenethyl, trityl, diphenylmethyl, 3,4-dimethoxyphenyl, phenyl, 4-chlorophenyl, tolyl and tert.-butylphenyl.

Examples of R' as an amino protective group are alkyl of 1 to 6 carbon atoms, preferably tert.-butyl and tert.-amyl, acyl of an aliphatic, aromatic or heterocyclic acid, or carbamoyl preferably a lower alkanoyl such as formyl, acetyl, propionyl, butyryl, isobutyryl, valeryl, isovaleryl, oxalyl, succinyl and pivaloyl; lower alkoxycarbonyl or cycloalkoxycarbonyl such as methoxycarbonyl, ethoxycarbonyl, propoxycarbonyl, 1-cyclopropylethoxycarbonyl, isopropoxycarbonyl, butyloxycarbonyl, tert.-butoxycarbonyl, pentyloxycarbonyl, hexyloxycarbonyl, benzoyl, toluolyl, naphthoyl, phthaloyl, mesyl, phenylacetyl, phenylpropionyl and aryloxycarbonyl such as benzyloxycarbonyl. The acyl group may be substituted such as with chlorine, bromine, iodine or fluorine like chloroacetyl, dichloroacetyl, trichloroacetyl, bromoacetyl and trifluoroacetyl.

R' may be a lower alkyl of 1 to 6 alkyl carbon atoms such as benzyl, 4-methoxy-benzyl, phenethyl, trityl, 3,4-dimethoxy-benzyl or benzhydryl; halo lower alkyl such as trichloroethyl; chlorobenzoyl, p-nitro-benzoyl, p-tert.-butylbenzoyl, phenoxyacetyl, caprylyl, n-decanoyl, acryloyl, trichloroethoxycarbonyl; methylcarbamoyl, phenylcarbamoyl, naphthylcarbamoyl and the corresponding thiocarbamoyls. The list is not intended to be exhaustive and other known amine protective groups may be used such as known in peptide synthesis.

The hydroxyl protective group of R" may be an acyl such as formyl, acetyl, chloroacetyl, bromoacetyl, dichloroacetyl, trichloroacetyl, trifluoroacetyl, methoxyacetyl, phenoxyacetyl, benzoyl, benzoylformyl, p-nitrobenzyl; ethoxycarbonyl, methoxycarbonyl, propoxycarbonyl, β,β,β-trichloroethoxycarbonyl, benzyloxycarbonyl, tert.-butoxycarbonyl, 1-cyclopropylethoxycarbonyl, tetrahydropyranyl, tetrahydrothiopyranyl, methoxytetrahydropyranyl, trityl, benzyl, 4-methoxybenzyl, benzhydryl, trichloroethyl, 1-methyl-1-methoxy ethyl or phthaloyl; propionyl, butyryl, isobutyryl, valeryl, isovaleryl, oxalyl, succinyl and pivaloyl; phenylacetyl, phenylpropionyl, mesyl, chlorobenzoyl, p-nitrobenzoyl, p-tert.-butylbenzoyl, caprylyl, acryloyl, methylcarbamoyl, phenylcarbamoyl and naphthylcarbamoyl.

In a preferred mode of the process of the invention, the compound of formula II is reacted with a functional derivative of the acid of formula III such as the acid halide symetrical acid anhydride, mixed anhydride, amide or active ester.

Examples of mixed anhydrides are those formed with isobutyl chloroformate or with pivaloyl chloride or mixed anhydrides with sulfonic acids-carboxylic acids such as with p-toluene sulfonyl chloride. An example of an active ester is that formed with 2,4-dinitrophenol or hydroxybenzothiazole. The acid halide is preferably the acid chloride or acid bromide. Also useful are the acid azide or the acid amide. The acid anhydride may be formed in situ by reaction with a disubstituted N,N'-carbodiimide such as dicyclohexylcarbodiimide.

The acylation reaction is preferably effected in an organic solvent such as methylene chloride although other organic solvents such as acetone, tetrahydrofuran, chloroform or dimethylformamide may be used. When an acid halide is used, the reaction is preferably effected with a base to react with the hydrogen halide formed such as sodium hydroxide, potassium hydroxide, sodium carbonate, sodium bicarbonate, potassium carbonate, potassium bicarbonate, sodium acetate, triethylamine, pyridine, morpholine and N-methylmorpholine and the reaction temperature is preferably held at room temperature or lower. When R' is hydrogen, the mixed carboxylicsulfonic acid anhydride is preferably used.

Depending on the values of R', R" and A, the compounds of formula IV may or may not be within the scope of the compounds of formula I. The compounds of formula IV are within the scope of formula I when R' is hydrogen, R" is not a hydroxyl protective group which is desired to be eliminated, for example 1-methoxyethyl and A is not among the easily cleavable tyl may be removed by reaction with thiourea in a neutral or acid medium by the reaction described by Masaki, J.A.C.S., Vol. 90 (1968), p. 4508. Other methods of removal of protective groups described in the literature may also be used.

Among the preferred groups of R' are formyl, acetyl, ethoxycarbonyl, mesyl, trifluoroacetyl, chloroacetyl and trityl with the last 2 being most preferred. The preferred acid used is trifluoroacetic acid.

The removal of A and R" when it is necessary may be effected under conditions similar for the removal of the R' groups. Acid hydrolysis is preferably used to remove optionally substituted alkyl or aralkyl groups and the preferred acids are hydrochloric acid, formic acid, trifluoroacetic acid and p-toluene sulfonic acid. Other values of A and R" may be removed, when desired, by methods known to one skilled in the art and the preferred conditions are moderate such as at room temperature or with slight heating.

Naturally when R' and A or R" are groups which are removable by different processes, the compounds of formula IV are subjected to reaction with a plurality of the above reagents or procedures.

The salification of the compounds of the invention is effected by usual methods by reacting the compound in its free acid form or as a solvate such as its ethanolate or or acetone and the salts obtained are in either an amorphous form or crystalline form depending on the reaction conditions used. Crystalline salts are preferably prepared by reacting the free acids with salts of the aliphatic carboxylic acids mentioned above and especially with sodium acetate.

The formation of the non-toxic, pharmaceutically acceptable acid addition salts is effected in the usual manner by reacting approximately stoichiometric amounts of the free base and the acid.

The eventual esterification of the compounds of formula I may be effected in the classical manner, generally by reacting an acid of formula I with a compound of the formula Z-Re wherein Z is —OH or a halogen such as chlorine, bromine or iodine and Re is an ester group of the non-exhaustive list discussed above. In certain cases, it is advantageous to effect the esterification with a product having an amino group which is blocked before removing the amino protective group.

The optional resolution of the compounds of formula II or IV may be effected with an optically active organic carboxylic acid or organic sulfonic acid such as tartaric acid, dibenzoyltartaric acid, camphosulfonic acid or glutamic acid and then decomposing the resulting salt by reaction with a mineral base such as sodium bicarbonate or an organic base such as a tertiary amine like triethylamine. Also, one may optionally employ optically active base.

In a preferred mode of the process of the invention for the preparation of compounds of formula I, one uses a compound of formula III wherein R" is hydrogen, a hydroxyl protective group or alkyl of 1 to 3 carbon atoms optionally substituted with a free, esterified or salified carboxyl group or a protected amino group and the compound of formula II used has X as sulfur and $R_1$ as hydrogen. Especially preferred are compounds of formula III wherein R' is an amino protective group and functional derivative is a symetrical anhydride or a mixed sulfonic acid-carboxylic acid anhydride. The preferred mixed anhydride is formed with p-toluene sulfonic acid and the R' protective group is preferably trityl.

The novel antibacterial compositions of the invention are comprised of an antibacterically effective amount of at least one compound of formula I and their non-toxic, pharmaceutically acceptable acid addition salts and an inert pharmaceutical carrier or excipient. The compositions may be in the form of tablets, dragees, gelules, granules, suppositories, injectable solutions or suspensions, pomades, creams or gels prepared in the classical manner.

Examples of suitable excipients are talc, arabic gum, lactose, starch, magnesium stearate, cacao butter, aqueous or non-aqueous vehicles, fatty bodies of animal or vegetable origin, paraffinic derivatives, glycols, diverse wetting agents, dispersants or emulsifiers and preservatives. The compositions may also be in powder form ready for dissolution in an appropriate vehicle such as sterile apyrogen water just before use.

The compositions of the invention have a very good antibiotic effect against gram negative bacteria such as coliform bacteria, klebsiella, salmonella and proteus bacteria and are useful for the treatment of colibacilloses and associated infections, proteus infections, and infections of klebsiella and Salmonella as well as other affections caused by gram negative bacteria. They are also useful for disinfection of surgical instruments.

Among the preferred compositions of the invention are those wherein R is hydrogen or alkyl of 1 to 3 carbon atoms optionally substituted with carboxyl which may be free, salified or esterified or with —$NH_2$, those wherein X is sulfur and those wherein $R_1$ is hydrogen and their non-toxic, pharmaceutically acceptable acid addition salts.

Preferred specific compounds of the invention are the syn isomers of 7-[2-(2-amino-4-thiazolyl)-2-methoxyimino-acetamido]-8-oxo-4-thia-1-azabicyclo(4,2,0)oct-2-ene-2-carboxylic acid, 7-[2-(2-amino-4-thiazolyl)-2-hydroxyiminoacetamido]-8-oxo-4-thia-1-azobicyclo [4,2,0] oct-2-ene-2-carboxylic acid and 7-[2-(2-amino-4-thiazolyl)-2-carboxymethoxyiminoacetamido]-8-oxo-4-thia-1-azabicyclo [4,2,0] oct-2-ene-2-carboxylic acid in their optically active or racemic mixture form and their alkali metal, alkaline earth metal, ammonium and organic amine salts and their easily cleavable esters, and salts with acids.

The novel method of the invention for combatting bacterial infections in warm-blooded animals, including humans, comprises administering to warm-blooded animals an antibacterially effective amount of at least one compound of formula I and their non-toxic, pharmaceutically acceptable acid addition salts. The compounds may be administered orally, rectally, parenterally (intramuscularly) or by topical application to the skin or mucous. The usual effective dose of the compounds will vary depending on the specific compound, method of administration and the treated infection but may vary from 0.003 to 0.05 mg/kg per day and especially 0.003 to 0.05 mg/kg orally or 0.007 to 0.01 mg/kg intramuscularly.

The novel intermediates of the invention are optically active or racemates of syn compounds of the formula

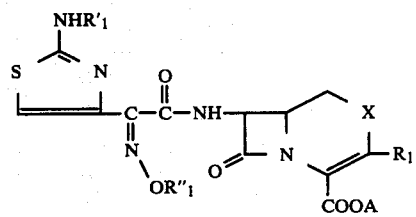

wherein $R_1$, A and X have the above definitions and $R_1'$ is an amino protective group and $R_1''$ is R" or $R_1'$ is hydrogen and $R_1''$ is a hydroxyl protective group.

The starting materials of formula II are described in the literature or can be easily prepared from known products. The compounds of formula II wherein X is sulfur are described in U.S. Pat. No. 4,166,816 and the oxidized sulfur compounds in the sulfoxide or sulfonic form are described in Can. J. Chem., Vol. 55 No. 15 (1977), p. 2873-2884. The compounds of formula II wherein X is oxygen are described in Can. J. Chem., Vol. 56 (1978), p. 2879 and 1335-1341 and in Belgium patent No. 837,265.

The compounds of formula III are described in the literature such as Belgium patent No. 850,662, No. 865,298 and No. 875,217. Mixed sulfonic acid-carboxylic acid anhydrides of formula III are described in European patent No. EP 0023453.

In the following examples there are described several preferred embodiments to illustrate the invention. However, it is to be understood that the invention is not intended to be limited to the specific embodiments.

EXAMPLE 1

Syn isomer of (6RS, 7RS)
7-[2-(2-amino-4-thiazolyl)-2-(methoxyimino)-
acetamido]-8-oxo-4-thia-1-azabicyclo [4,2,0]
oct-2-ene-2-carboxylic acid

STEP A: Syn isomer of sodium 7-[2-(2-tritylamino-4-thiazolyl)-2-methoxyimino-acetamido]-8-oxo-4-thia-1-azabicyclo [4,2,0] oct-2-ene-2-carboxylate A mixture of 540 mg of the triethylamine salt of the syn isomer of 2-(2-tritylamino-thiazol-4-yl)-2-methoxyimino-acetic acid, 188 mg of tosyl chloride and 6.4 ml of acetone was stirred under an inert atmosphere for one hour to form solution A.

Extemparaneously prepared was a solution of 180 mg of 7-amino-8-oxo-4-thia-1-azabicyclo [4,2,0]-oct-2-ene-2-carboxylic acid in 2 ml of 1 molar aqueous sodium bicarbonate solution and 1 ml of water and the mixture was cooled in iced water. Solution A was added thereto dropwise and the mixture was rinsed with acetone and removed from the iced water bath. The mixture was stirred at room temperature for 80 minutes and was vacuum filtered. The recovered product was rinsed with acetone and dried to obtain 297 mg of syn isomer of sodium 7-[2-(2-tritylamino-4-thiazolyl)-2-methoxyiminoacetamido]-8 -oxo-4-thia-1-azabicyclo [4,2,0] oct-2-ene-2-carboxylate.

STEP B: Syn isomer of (6RS, 7RS) 7-[2-(2-amino-4-thiazolyl)-2-methoxyimino-acetamido]-8-oxo-4-thia-1-azabicyclo [4,2,0] oct-2-ene-2-carboxylic acid The 297 mg of the product of Step A were suspended in 1.5 ml of aqueous 66% formic acid solution and the mixture was stirred at 50° C. for 15 minutes and was then cooled to room temperature. 0.66 ml of water were added to the mixture which was then filtered and the filter was rinsed with water. A little ethanol was added to the filtrate which was then evaporated to dryness under reduced pressure. The oil residue was taken up in water and ethanol and the mixture was again evaporated to dryness. The residue was added to 2 ml of a 1 M solution of sodium bicarbonate solution and 1.65 ml of water to form a solution which was then filtered. 2 N hydrochloric acid was added to the mixture to adjust the pH to 3 and a little ethanol was added thereto. After crystallization, the mixture was filtered and the product was rinsed with water and then with ether and dried to obtain 102 mg of syn isomer of (6RS, 7RS) 7-[2-(2-amino-4-thiazolyl)-2-methoxyimino-acetamido]-8-oxo-4-thia-1-azabicyclo [4,2,0] oct-2-ene-2-carboxylic acid NMR Spectrum (DMSO): Peaks at 3.88 ppm (hydrogens of NOCH$_3$); at 5.69 ppm (dd) (7$\alpha$-hydrogen J=5 HZ); at 6.85 ppm (5-hydrogen of thiazolesyn isomer).

EXAMPLE 2

Syn isomer of (6RS, 7RS)
7-[2-(2-amino-4-thiazolyl)-2-hydroxyimino-acetamido]-
8-oxo-4-thia-1-azabicyclo [4,2,0] oct-2-ene-2-carboxylic
acid

STEP A: Syn isomer of tert.-butyl (6RS, 7RS) 7-[2-(2-tritylamino-4-thiazolyl)-2-/(1-methyl-1-methoxyethoxy) imino/acetamido]-8-oxo-4-thia-1-azabicyclo [4,2,0] oct-2-ene-2-carboxylate 0.135 ml of triethylamine was added under an inert atmosphere to a solution of 230 mg of tert.-butyl (6RS, 7RS) 7-amino-8-oxo-4-thia-1-azabicyclo [4,2,0] oct-2-ene-2-carboxylate in 2.5 ml of methylene chloride and then 814 mg of a mixed anhydride of p-toluenesulfonic acid and syn isomer 2-(2-tritylamino-4-thiazolyl)-2-(1-methyl-1-methoxyethoxy)imino acetic acid with an equivalent of triethylamine hydrochloride were added thereto. The mixture was stirred for 45 minutes and then 2 drops of acetic acid were added followed by water addition. The mixture was stirred and the decanted aqueous phase was extracted with methylene chloride. The combined organic phases were dried and evaporated to dryness to obtain syn isomer of tert.-butyl (6RS, 7RS) 7-[2-(2-tritylamino-4-thiazolyl)-2-/(1-methyl-1-methoxyethoxy)-imino/-acetamido]-8-oxo-4-thia-1-azabicyclo [4,2,0] oct-2-ene-2-carboxylate in the form of a resin.

STEP B: Syn isomer of (6RS, 7RS) 7-[2-(2-amino-4-thiazolyl)-2-hydroxyimino-acetamido]-8-oxo-4-thia-1-azabicyclo [4,2,0] oct-2-ene-2-carboxylic acid A solution of the resin of Step A in 3.2 ml of trifluoroacetic acid stood for 25 minutes and then 32 ml of isopropyl ether were added thereto. The mixture was filtered and the recovered product was rinsed with isopropyl ether, dried and added to 2 ml of an aqueous 10% sodium bicarbonate solution. The mixture was stirred and filtered and the filter was rinsed with water. The filtrate was adjusted to a pH of 4.5 by addition of 2 N hydrochloric acid to obtain a yellow precipitate and the mixture was stirred for 10 minutes and was vacuum filtered. The product was rinsed with water to obtain a first yield of 64 mg of product. The pH of the filtrate was adjusted to 4 and crystallization was induced. The mixture was stirred for 10 minutes and was vacuum filtered and to obtain 61 mg of product to form a total yield of 125 mg of syn isomer of (6RS,7RS) 7-[2-(2-amino-4-thiazolyl)-2-hydroxyimino-acetamido]-8-oxo-4-thia-1-azabicyclo [4,2,0] oct-2-ene-2-carboxylic acid.

NMR Spectrum (DMSO): Peaks at 3.16 ppm (hydrogens of —S—CH$_2$—); at 5.66 ppm (dd) (7$\alpha$-hydrogen)(J=5 Hz); at 6.76 ppm (5-hydrogen of thiazolsyn isomer).

EXAMPLE 3

Syn isomer of (6RS, 7RS)
7-[2-(2-amino-4-thiazolyl)-2-carboxymethoxyimino-
acetamido]-8-oxo-4-thia-1-azabicyclo [4,2,0]
oct-2-ene-2-carboxylic acid

STEP A: Syn isomer of tert.-butyl (6RS, 7RS) 7-[2-(2-tritylamino-4-thiazolyl)-2-tert.-butoxycarbonyl-methoxyimino-acetamido]-8-oxo-4-thia-1-azabicyclo [4,2,0] oct-2-ene-2-carboxylate A mixture of 957 mg of the syn isomer of 2-(2-tritylamino-4-thiazolyl)-2-(tert.-butoxycarbonylmethoxyimino)acetic acid, 217 mg of dicyclohexylcarbodiimide and 15 ml of methylene chloride was stirred under an inert atmosphere for 30 minutes and then 225 mg of tert.-butyl (6RS, 7RS) 7-amino-8-oxo-4-thia-1-azabicyclo [4,2,0] oct-2-ene-2-carboxylate were added thereto. The mixture stood at room temperature for one hour and was filtered to remove dicyclohexylurea. The filtrate was evaporated to dryness under reduced pressure and the residue was added to a mixture of ethyl acetate and 4 ml of aqueous 10% sodium bicarbonate solution. The mixture was stirred and vacuum filtered.

The recovered product was rinsed with ethyl acetate and was empasted twice with methylene chloride and filtered. The filtrate was evaporated to dryness and the residue was added to ethyl acetate. The combined ethyl acetate phases were washed with water and the wash water was extracted with ethyl acetate. The combined ethyl acetate phases were dried and evaporated to dryness to obtain 838 mg of syn isomer of tert.-butyl (6RS, 7RS) 7-[2-(2-tritylamido-4-thiazolyl)-2-tert.-butoxycarbonylmethoxyimino-acetamino]-8-oxo-4-thia-1-azabicyclo [4,2,0] oct-2-ene-2-carboxylate in the form of a resin.

STEP B: Syn isomer of (6RS, 7RS) 7-[2-(2-amino-4-thiazolyl)-2-carboxymethoxyimino-acetamido]-8-oxo-4-thia-1-azabicyclo [4,2,0] oct-2-ene-2-carboxylic acid A solution of the resin of Step A in 4 ml of trifluoroacetic acid stood for 20 minutes and 40 ml of isopropyl ether were added thereto. The mixture was filtered and the filter was rinsed and evaporate to dryness. The product was taken up in 1.5 ml of a molar aqueous solution of sodium bicarbonate and activated carbon was added to the mixture. The mixture was vacuum filtered and the filter was rinsed with water. The product was added to 2 N hydrochloric acid to obtain a pH of 3 to 4 to obtain a precipitate and the mixture was vacuum filtered. The product was rinsed with water and dried to obtain a first yield of 78 mg of product. 2 N hydrochloric acid was added dropwise to the mother liquors and the mixture was vacuum filtered to obtain a semi-crystalline product which was washed and dried to obtain a second yield of 30 mg of product. The 2 yields were combined and homogenized to obtain 108 mg of syn isomer of (6RS, 7RS) 7-[2-(2-amino-4-thiazolyl)-2-carboxymethoxyimino-acetamido]-8-oxo-4-thia-1-azabicyclo [4,2,0] oct-2-ene-2-carboxylic acid.

NMR Spectrum (DMSO): Peaks at 4.63 ppm (hydrogens of N—O—CH$_2$—COOH); at 5.71 ppm (d,d) (7α-hydrogen); at 6.88 ppm (5-hydrogen of thiazolesyn isomer)

EXAMPLE 4

An injectable preparation was prepared containing 500 mg of either the syn isomer of (6RS, 7RS) 7-[2-(2-amino-4-thiazolyl)-2-methoxyimino-acetamido]-8-oxo-4-thia-1-azabicyclo [4,2,0] oct-2-ene-2-carboxylic acid or the syn isomer of (6RS, 7RS) 7-[2-(2-amino-4-thiazolyl)-2-carboxymethoxyiminoacetamido]-8-oxo-4-thia-1-azabicyclo [4,2,0] oct-2-ene-2-carboxylic acid and sufficient sterile aqueous excipient for a final volume of 5 ml.

Gelules were prepared containing 250 mg of the syn isomer of (6RS, 7RS) 7-[2-(2-amino-4-thiazolyl)-2-hydroxyimino-acetamido]-8-oxo-4-thia-1-azabicyclo [4,2,0] oct-2-ene-2-carboxylic acid and sufficient excipient for a final weight of 400 mg.

EXAMPLE 5

Examples of other compounds of formula I which may be prepared by the process of the invention are set forth in the following Table which indicates the compounds wherein X, R, A and $R_1$ have the values therein.

| X | R | A | $R_1$ |
|---|---|---|---|
| S | $\begin{array}{c} CH_3 \\ \| \\ C-CO_2H \\ \| \\ CH_3 \end{array}$ | H | H |
| S | $CH_3$ | $CH_2-O-\underset{\underset{O}{\|\|}}{C}-CH_3$ | H |
| S | $CH_3$ | $CH_2-O-\underset{\underset{O}{\|\|}}{C}-CH_2-CH_3$ | H |
| S | $CH_3$ | $\begin{array}{c} CH-O-\underset{\underset{O}{\|\|}}{C}-CH_3 \\ \| \\ CH_3 \end{array}$ | H |
| S | $CH_3$ | $CH_2-O-\underset{\underset{O}{\|\|}}{C}-OCH_3$ | H |
| S | H | $CH_2-O-\underset{\underset{O}{\|\|}}{C}-CH_3$ | H |
| S | H | $CH_2-O-\underset{\underset{O}{\|\|}}{C}-C_2H_5$ | H |
| S | H | $\begin{array}{c} CH-O-\underset{\underset{O}{\|}}{C}-CH_3 \\ \| \\ CH_3 \end{array}$ | H |
| S | H | $CH_2-O-\underset{\underset{O}{\|\|}}{C}-OCH_3$ | H |
| S | H | H | $CH_2-O-\underset{\underset{O}{\|\|}}{C}-CH_3$ |

-continued

| X | R | A | R₁ |
|---|---|---|---|
| S | H | H | CH₃ |
| S | CH₃ | H | CH₂—O—C(=O)—CH₃ |
| S | CH₃ | H | CH₃ |
| S | CH₂—CO₂H | H | CH₂—O—C(=O)—CH₃ |
| S | CH₂—CO₂H | H | CH₃ |
| S | H | CH₂—O—C(=O)—C₂H₅ | CH₂—O—C(=O)—CH₃ |
| S | H | CH₂—O—C(=O)—C₂H₅ | CH₃ |
| S | H | CH(CH₃)—O—C(=O)—CH₃ | CH₂—O—C(=O)—CH₃ |
| S | H | CH(CH₃)—O—C(=O)—CH₃ | CH₃ |
| S | H | CH₂—O—C(=O)—OCH₃ | CH₂—O—C(=O)—CH₃ |
| S | H | CH₂—O—C(=O)—OCH₃ | CH₃ |
| S→O | H | H | H |
| S→O | CH₃ | H | H |
| S→O | CH₂—CO₂H | H | H |
| S→O | C(CH₃)₂—CO₂H | H | H |
| S→O | H | H | CH₂—O—C(=O)—CH₃ |
| S→O | CH₃ | H | CH₃ |
| S→O | H | H | CH₃ |
| S→O | CH₃ | H | CH₂—O—C(=O)—CH₃ |
| S→O | CH₂—CO₂H | H | CH₂—O—C(=O)—CH₃ |
| S→O | CH₂—CO₂H | H | CH₃ |
| S→O | C(CH₃)₂—CO₂H | H | CH₂—O—C(=O)—CH₃ |

-continued

| X | R | A | R₁ |
|---|---|---|---|
| | $\begin{array}{c}CH_3\\|\\C-CO_2H\\|\\CH_3\end{array}$ | H | CH₃ |
| S→O | H | CH₂—O—C(=O)—C₂H₅ | H |
| S→O | CH₃ | CH₂—O—C(=O)—C₂H₅ | H |
| S→O | H | CH(CH₃)—O—C(=O)—CH₃ | H |
| S→O | CH₃ | CH(CH₃)—O—C(=O)—CH₃ | H |
| S→O | H | CH₂—O—C(=O)—O—CH₃ | H |
| S→O | CH₃ | CH₂—O—C(=O)—O—CH₃ | H |
| S→O | H | CH₂—O—C(=O)—C₂H₅ | CH₃ |
| S→O | H | CH(CH₃)—O—C(=O)—CH₃ | CH₃ |
| S→O | H | CH₂—O—C(=O)—O—CH₃ | CH₃ |
| S→O | CH₃ | CH₂—O—C(=O)—C₂H₅ | CH₂—O—C(=O)—CH₃ |
| S→O | CH₃ | CH(CH₃)—O—C(=O)—CH₃ | CH₂—O—C(=O)—CH₃ |
| S→O | CH₃ | CH₂—O—C(=O)—O—CH₃ | CH₂—O—C(=O)—CH₃ |
| O | H | H | H |
| O | CH₃ | H | H |
| O | CH₂—CO₂H | H | H |
| O | $\begin{array}{c}CH_3\\|\\C-CO_2H\\|\\CH_3\end{array}$ | H | H |
| O | H | H | CH₂—O—C(=O)—CH₃ |
| O | CH₃ | H | CH₃ |
| O | H | H | CH₃ |
| O | CH₃ | H | CH₂—O—C(=O)—CH₃ |
| O | CH₂—CO₂H | H | CH₂—O—C(=O)—CH₃ |
| O | CH₂—CO₂H | H | CH₃ |

-continued

| X | R | A | $R_1$ |
|---|---|---|---|
| O | $\underset{CH_3}{\underset{|}{\overset{CH_3}{\overset{|}{C}}}}-CO_2H$ | H | $CH_2-O-\underset{O}{\overset{\|}{C}}-CH_3$ |
| O | $\underset{CH_3}{\underset{|}{\overset{CH_3}{\overset{|}{C}}}}-CO_2H$ | H | $CH_3$ |
| O | H | $CH_2-O-\underset{O}{\overset{\|}{C}}-C_2H_5$ | H |
| O | $CH_3$ | $CH_2-O-\underset{O}{\overset{\|}{C}}-C_2H_5$ | H |
| O | H | $\underset{CH_2}{\underset{|}{CH}}-O-\underset{O}{\overset{\|}{C}}-CH_3$ | H |
| O | $CH_3$ | $\underset{CH_3}{\underset{|}{CH}}-O-\underset{O}{\overset{\|}{C}}-CH_3$ | H |
| O | H | $CH_2-O-\underset{O}{\overset{\|}{C}}-OCH_3$ | H |
| O | $CH_3$ | $CH_2-O-\underset{O}{\overset{\|}{C}}-OCH_3$ | H |
| O | H | $CH_2-O-\underset{O}{\overset{\|}{C}}-C_2H_5$ | $CH_3$ |
| O | H | $\underset{CH_3}{\underset{|}{CH}}-O-\underset{O}{\overset{\|}{C}}-CH_3$ | $CH_3$ |
| O | H | $CH_2-O-\underset{O}{\overset{\|}{C}}-OCH_3$ | $CH_3$ |
| O | $CH_3$ | $CH_2-O-\underset{O}{\overset{\|}{C}}-C_2H_5$ | $CH_2-O-\underset{O}{\overset{\|}{C}}-CH_3$ |
| O | $CH_3$ | $\underset{CH_3}{\underset{|}{CH}}-O-\underset{O}{\overset{\|}{C}}-CH_3$ | $CH_2-O-\underset{O}{\overset{\|}{C}}-CH_3$ |
| O | $CH_3$ | $CH_2-O-\underset{O}{\overset{\|}{C}}-OCH_3$ | $CH_2-O-\underset{O}{\overset{\|}{C}}-CH_3$ |

PHARMACOLOGICAL DATA

The antibacterial activity was determined in vitro by the method of dilution with a liquid medium. A series of tubes were prepared by placing the same amount of sterile nutritive medium therein and an increasing amount of the test product was added to each tube. Then, each tube was seeded with a bacterial strain and incubated in an oven at 37° C. for 24 or 48 hours. The inhibition in the growth was determined by transillumination to determine the minimum inhibitory concentration in μg/ml and the results are in the following Tables.

| | Product of Example 1 | |
|---|---|---|
| | M.I.C. in μg/ml | |
| STRAINS | 24 H | 48 H |
| *Escherichia Coli* Sensible Tetracycline 7624 | 0,2 | 0,5 |
| *Escherichia Coli* Resistant Tetracycline ATCC 11 303 | 0,05 | 0,1 |
| *Escherichia Coli* Exp. $TO_{26}B_6$ | 0,2 | 0,2 |
| *Escherichia Coli* Resistant Gentamicine Tobramycine R 55 123 D | 0,2 | 0,2 |
| *Klebsiella pneumoniae* Exp. 52 145 | 0,05 | 0,05 |
| *Klebsiella pneumoniae* 2 536 Resistant Gentamycine | 0,2 | 0,5 |
| *Proteus mirabilis* (indol−) A 235 | ≦0,02 | 0,05 |
| *Proteus vulgaris* (indol+) A 232 | 0,05 | 0,02 |

-continued

Product of Example 1

| STRAINS | M.I.C. in µg/ml | |
|---|---|---|
| | 24 H | 48 H |
| *Salmonella typhimurium* 420 | 0,5 | 0,5 |
| Providencia Du 48 | 0,1 | 0,2 |
| Serratia Resistant Gentamicine 2 532 | 1 | 2 |

Product of Example 2

| *Escherichia Coli* Sensible Tetracycline 7624 | 0,3 | 0,3 |
|---|---|---|
| *Escherichia Coli* Resistant Tetracycline ATCC 11 303 | 0,3 | 0,3 |
| *Escherichia Coli* Resistant Gentamicine, Tobramycine R 55 123 D | 0,6 | 0,6 |
| *Klebsiella pneumoniae* Exp. 52 145 | 0,6 | 0,6 |
| *Klebsiella pneumoniae* 2 536 Resistant Gentamycine | 1,25 | 1,25 |
| *Proteus mirabilis* (indol−) A 235 | 0,6 | 0,6 |
| *Proteus vulgaris* (indol+) A 232 | 0,3 | 0,3 |
| Providencia Du 48 | 0,15 | 0,15 |

Product of Example 3

| *Escherichia Coli* Sensible Tetracycline 7624 | 2,5 | 2,5 |
|---|---|---|
| *Escherichia Coli* Resistant Tetracycline ATCC 11 303 | 0,08 | 0,08 |
| *Escherichia Coli* Resistant Gentamicine Tobramycine R 55 123 D | 2,5 | 2,5 |
| *Klebsiella pneumoniae* Exp. 52 145 | 0,15 | 0,15 |
| *Klebsiella pneumoniae* 2 536 Resistant Gentamycine | 0,3 | 0,3 |
| *Proteus mirabilis* (indol−) A 235 | 0,08 | 0,08 |
| *Proteus vulgaris* (indol+) A 232 | 0,04 | 0,08 |
| *Salmonella typhimurium* 420 | 0,3 | 0,6 |
| Providencia Du 48 | 0,08 | 0,08 |

The results of the Tables show the antibacterial activity of the compounds of Examples 1 to 3.

Various modifications of the products and processes of the invention may be made without departing from the spirit or scope thereof and it is to be understood that the invention is intended to be limited only as defined in the appended claims.

What we claim is:

1. A compound selected from the group consisting of syn isomers of optically active isomers and racemates of 7-[2-(2-amino-4-thiazolyl)-2-oxyimino-acetamido]-bicyclooctene-carboxylic acid derivatives of the formula

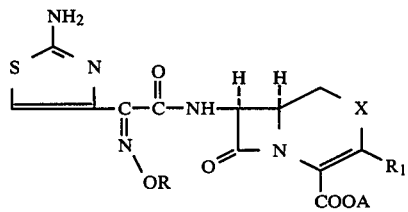

wherein R is selected from the group consisting of hydrogen, optionally substituted alkyl of 1 to 6 carbon atoms and optionally substituted alkenyl and alkynyl of 2 to 6 carbon atoms, $R_1$ is selected from the group consisting of hydrogen, methyl, halomethyl, hydroxymethyl and acyloxymethyl of an organic carboxylic acid of 1 to 7 carbon atoms, X is optionally oxidized sulfur, A is selected from the group consisting of hydrogen, an alkali metal, —$NH_4$, alkaline earth metal equivalent, a non-toxic, pharmaceutically acceptable organic amine and an easily cleavable ester group and their non-toxic, pharmaceutically acceptable acid addition salts, the optional substituents being selected from the group consisting of optionally salified or esterified carboxyl, alkoxycarbonyl, carbamoyl, dimethylcarbamoyl, amino, dialkylamino of 1 to 6 alkyl carbons, alkylamino of 1 to 6 alkyl carbons, halogens, alkoxy and alkylthio of 1 to 6 carbon atoms, tetrazolyl, optionally alkyl substituted phenylthio, optionally alkyl substituted tetrazolylthio and thiadiazolylthio wherein the alkyl is 1 to 6 carbon atoms.

2. A compound of claim 1 wherein R is selected from the group consisting of hydrogen, amino and alkyl of 1 to 3 carbon atoms optionally substituted with a free, salified or esterified carboxyl, X is sulfur and $R_1$ is hydrogen.

3. A compound of claim 1 which is selected from the group consisting of optically active isomers and racemic mixtures of syn isomer of 7-[2-(2-amino-4-thiazolyl)-2-methoxyimino-acetamido]-8-oxo-4-thia-1-azabicyclo [4,2,0] oct-2-ene-2-carboxylic acid and its alkali metal, alkaline earth metal, ammonium, magnesium and organic amine salts and easily cleavable esters, and salts with acids.

4. A compound of claim 1 which is selected from the group consisting of optically active isomers and racemic mixtures of syn isomer of 7-[2-(2-amino-4-thiazolyl)-2-hydroxyimino-acetamido]-8-oxo-4-thia-1-azabicyclo [4,2,0] oct-2-ene-2-carboxylic acid and its alkali metal, alkaline earth metal, ammonium, magnesium and organic amine salts and easily clevable esters, and salts with acids.

5. A compound of claim 1 which is selected from the group consisting of optically active isomers and racemic mixtures of syn isomer of 7-[2-(2-amino-4-thiazolyl)-2-carboxymethoxyimino-acetamido]-8-oxo-4-thia-1-azabicyclo [4,2,0] oct-2-ene-2-carboxylic acid and its alkali metal, alkaline earth metal, ammonium, magnesium and organic amine salts and easily clevable esters, and salts with acids.

6. A syn isomer of a compound of the formula

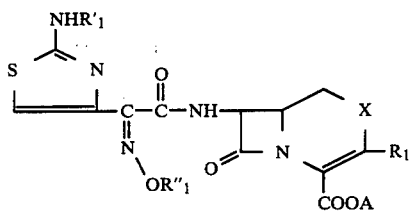

wherein $R_1$, A and X have the definitions of claim 1, $R'_1$ is an amino protective group and $R''_1$ is selected from the group consisting of hydroxyl protective group and R as defined in claim 1 or $R'_1$ is hydrogen and $R''_1$ is a hydroxyl protective group in its optically active isomeric form or racemic mixtures thereof.

7. An antibacterial composition comprising an antibacterially effective amount of at least one compound of claim 1 and an inert pharmaceutical carrier.

8. A composition of claim 7 wherein R is selected from the group consisting of hydrogen, amino and alkyl of 1 to 3 carbon atoms optionally substituted with a free, salified and esterified carboxyl, X is sulfur and $R_1$ is hydrogen.

9. A composition of claim 7 wherein the compound is selected from the group consisting of optically active isomers and racemic mixtures of syn isomers of 7-[2-(2-amino-4-thiazolyl)-2-methoxyimino-acetamido]-8-oxo-4-thia-1-azabicyclo [4,2,0] oct-2-ene-2-carboxylic acid and its alkali metal, alkaline earth metal, ammonium, magnesium and organic amine salts and easily cleavable esters, and salts with acids.

10. A composition of claim 7 wherein the compound is selected from the group consisting of optically active isomers and racemic mixtures of syn isomers of 7-[2-(2-amino-4-thiazolyl)-2-hydroxyimino-acetamido]-8-oxo-4-thia-1-azabicyclo [4,2,0] oct-2-ene-2-carboxylic acid and its alkali metal, alkaline earth metal, ammonium, magnesium and organic amine salts and easily cleavable esters, and salts with acids.

11. A composition of claim 7 wherein the compound is selected from the group consisting of optically active isomers and racemic mixtures of syn isomers of 7-[2-(amino-4-thiazolyl)-2-carboxymethoxyimino-acetamido]-8-oxo-4-thia-1-azabicyclo [4,2,0] oct-2-ene-2-carboxylic acid and its alkali metal, alkaline earth metal, ammonium, magnesium, and organic amine salts and easily cleavable esters, and salts with acids.

12. A method of combatting bacterial infections in warm-blooded animals comprising administering to warm-blooded animals an antibacterially effective amount of at least one compound of claim 1.

13. A method of claim 12 wherein R is selected from the group consisting of hydrogen, amino and alkyl of 1 to 3 carbon atoms optionally substituted with a free, salified and esterified carboxyl, X is sulfur and $R_1$ is hydrogen.

14. A method of claim 12 wherein the compound is selected from the group consisting of optically active and racemic mixtures of syn isomers of 7-[2-(2-amino-4-thiazolyl)-2-methoxyimino-acetamido]-8-oxo-4-thia-1-azabicyclo [4,2,0] oct-2-ene-2-carboxylic acid and its alkali metal, alkaline earth metal, ammonium, magnesium and organic amine salts and easily cleavable esters, and salts with acids.

15. A method of claim 12 wherein the compound is selected from the group consisting of optically active and racemic mixtures of syn isomers of 7-[2-(2-amino-4-thiazolyl) -2-hydroxy-imino-acetamido] -8-oxo-4-thia-1-azabicyclo [4,2,0] oct-2-ene-2-carboxylic acid and its alkali metal, alkaline earth metal, ammonium, magnesium and organic amine salts and easily cleavable esters, and salts with acids.

16. A method of claim 12 wherein the compound is selected from the group consisting of optically active and racemic mixtures of syn isomers of 7-[2-(2-amino-4-thiazolyl)-2-carboxymethoxyimino-acetamido]-8-oxo-4-thia-1-azabicyclo [4,2,0] oct-2-ene-2-carboxylic acid and its alkali metal, alkaline earth metal, ammonium, magnesium and organic amine salts and easily cleavable esters, and salts with acids.

* * * * *